United States Patent
Steynberg et al.

(10) Patent No.: US 6,201,031 B1
(45) Date of Patent: Mar. 13, 2001

(54) PROCESS FOR PRODUCING LIQUID AND, OPTIONALLY, GASEOUS PRODUCTS FROM GASEOUS REACTANTS

(75) Inventors: Andr′′ Peter Steynberg, Vanderbijlpark; Herman Gerhardus Nel, Sasolburg, both of (ZA); Roy W. Silverman, Winchester, MA (US)

(73) Assignee: Sasol Technology (Proprietary) (Limited) (ZA)

( * ) Notice: Subject to any disclaimer, the term of this patent is extended or adjusted under 35 U.S.C. 154(b) by 0 days.

(21) Appl. No.: 09/454,849

(22) Filed: Dec. 7, 1999

Related U.S. Application Data

(63) Continuation of application No. PCT/GB98/02070, filed on Jul. 14, 1998.

(30) Foreign Application Priority Data

Jul. 15, 1997 (ZA) .................................................. 97/6254

(51) Int. Cl.$^7$ ................................................. C07C 27/00
(52) U.S. Cl. ......................................... 518/715; 518/700
(58) Field of Search ..................................... 518/715, 700

(56) References Cited

U.S. PATENT DOCUMENTS 5,962,537 * 10/1999 Leviness ............................. 518/700

* cited by examiner

Primary Examiner—Johanh Richter
Assistant Examiner—J. Parsa
(74) Attorney, Agent, or Firm—Ladas and Parry

(57) ABSTRACT

A process for producing liquid and/or gaseous products from gaseous reactants includes feeding them, at a low level, into a slurry bed of particles suspended in a liquid, to react as they rise therethrough to form the products, with the reactants and any gaseous product assisting in maintaining the suspension. The liquid product forms, together with the suspension liquid, the liquid phase of the bed. Any gaseous product and unreacted reactants rise from the bed into a head space. Slurry passes downwardly in the bed through downcomers located respectively in first and second downcomer regions of the bed, thereby redistributing solid particles within the bed. The second downcomer region is spaced vertically with respect to the first downcomer region. Any gaseous product and unreacted reactants are withdrawn from the head space and liquid phase is withdrawn from the bed.

11 Claims, 2 Drawing Sheets

PROCESS FOR PRODUCING LIQUID AND, OPTIONALLY, GASEOUS PRODUCTS FROM GASEOUS REACTANTS

This application is a continuation of PCT/GB98/0270 filed on Jul. 14, 1998.

THIS INVENTION relates to a process for producing liquid and, optionally, gaseous products from gaseous reactants. It relates also to an installation for producing liquid and, optionally, gaseous products from gaseous reactants.

According to a first aspect of the invention, there is provided a process for producing liquid and, optionally, gaseous products from gaseous reactants, which process comprises feeding, at a low level, gaseous reactants into a slurry bed of solid particles suspended in a suspension liquid;

allowing the gaseous reactants to react as they pass upwardly through the slurry bed, thereby to form liquid and, optionally, gaseous products, with the gaseous reactants and any gaseous product assisting in maintaining the solid particles in suspension in the suspension liquid, and with the liquid product forming, together with the suspension liquid, a liquid phase of the slurry bed;

allowing any gaseous product and unreacted gaseous reactants to disengage from the slurry bed into a head space above the slurry bed;

allowing slurry to pass downwardly from a high level in the slurry bed to a lower level thereof, through at least one dowrcomer located in a first downcomer region of the slurry bed, as well as through at least one further downcomer located in a second downcomer region of the slurry bed, with the second downcomer region being spaced vertically with respect to the first downcomer region, thereby to redistribute solid particles within the slurry bed;

withdrawing any gaseous product and unreacted gaseous reactants from the head space; and withdrawing liquid phase from the slurry bed, to maintain the slurry bed at a desired level.

While it is believed that the process can, at least in principle, have broader application, it is envisaged that the solid particles will normally be catalyst particles for catalyzing the reaction of the gaseous reactants into the liquid product, and, when applicable, the gaseous product; and the suspension liquid will normally, but not necessarily always, be the liquid product.

The slurry bed may thus be contained or provided in a reaction zone of a slurry reactor or bubble column. By passing or recirculating some of the slurry through the downcomers, more uniform redistribution of the catalyst in the slurry bed than would be the case without such downcomers, is achieved. The slurry reactor or bubble column thus uses a three phase system, ie solid catalyst particles, liquid product, and gaseous reactants and, optionally, product.

Furthermore, while it is also believed that, in principle, the process can have broader application, it is envisaged that it will have particular application in hydrocarbon synthesis where the gaseous reactants are capable of reacting catalytically in the slurry bed to form liquid hydrocarbon product and, optionally, gaseous hydrocarbon product. In particular, the hydrocarbon synthesis may be Fischer-Tropsch synthesis, with the gaseous reactants being in the form of a synthesis gas stream comprising mainly carbon monoxide and hydrogen, and with both liquid and gaseous hydrocarbon products being produced.

The Fischer-Tropsch synthesis reaction is highly exothermic, and the Applicant has surprisingly found that a more uniform distribution of heat is achieved by recirculating some of the slurry through the downcomers in the first and second vertically spaced downcomer regions, in accordance with the invention.

The catalyst of the catalyst particles can be any desired Fischer-Tropsch catalyst, such as an iron-based catalyst, a cobalt-based catalyst, or any other Fischer-Tropsch catalyst. The catalyst particles may have a desired particle size range, eg no catalyst particles greater than 300 microns and less than 5% by mass of the catalyst particles being smaller than 22 microns.

The slurry reactor or bubble column will thus be maintained at normal elevated pressure and temperature conditions associated with Fischer-Tropsch synthesis reactions, eg a predetermined operating pressure in the range 10 to 50 bar, and a predetermined temperature in the range 160° C. and 280° C., or even higher for the production of lower boiling point product.

The catalyst particles in the slurry bed are thus maintained in suspension by the turbulence created by the synthesis gas stream passing through the slurry bed, ie bubbling through the slurry bed. The gas velocity through the slurry bed is thus sufficiently high to maintain the slurry bed in a state of turbulence or suspension.

According to a second aspect of the invention, there is provided an installation for producing liquid and, optionally, gaseous products from gaseous reactants, the installation comprising a reactor vessel having a slurry bed zone which, in use, will contain a slurry bed of solid particles suspended in a suspension liquid;

a gas inlet in the vessel at a low level within the slurry bed zone, for introducing gaseous reactants into the vessel;

a gas outlet in the vessel above the slurry bed zone, for withdrawing unreacted gaseous reactants and, when present, gaseous product from the vessel;

at least one downcomer located in a first downcomer region in the slurry bed zone and through which, in use, slurry can pass downwardly;

at least one further downcomer located in a second downcomer region in the slurry bed zone, with the second downcomer region being spaced vertically relative to the first downcomer region, with slurry, in use, also passing downwardly through this downcomer; and a liquid outlet in the vessel within the slurry bed zone, for withdrawing liquid product from the vessel.

The downcomers or draft tubes are thus located at different levels or vertical elevations within the slurry bed or the slurry bed zone. The second downcomer region may be located at a higher level than the first downcomer region, and, if desired, further downcomer regions, each containing at least one downcomer or draft tube may be provided above the second downcomer region, with a third and any subsequent downcomer regions also being spaced vertically from one another.

In one embodiment of the invention, the second downcomer region may overlap the first downcomer region. In other words, the lower end(s) of the downcomer(s) in the second downcomer region may overlap the uppper end(s) of the downcomer(s) in the first downcomer region. In another embodiment of the invention, however, the second downcomer region may be located in non-overlapping relationship with respect to the first downcomer region. In other words, the lower end(s) of the downcomer(s) in the second downcomer region may be spaced with vertical clearance from the upper end(s) of the downcomer(s) in the first downcomer region.

The downcomer(s) in the second downcomer region may be staggered with respect to that(those) in the first downcomer region, when the reactor or vessel is seen in plan view. In other wards, the lower end(s) of the downcomer(s) in the second downcomer region preferably does(do) not discharge slurry directly above the upper end(s) of the downcomer(s) in the first downcomer region.

Each downcomer may comprise a lower transport section and an upper disengagement or degassing section of greater cross-sectional area than the transport section. The sections are preferably circular in cross-section, is of cylindrical form, with an outwardly upwardly flaring connecting component connecting the disengagement section to the transport section. However, the disengagement section can, if desired, be in another suitable form, eg in the form of a rectangular or triangular section channel, as determined by the space available inside the reactor vessel.

The process may include operating the slurry reactor such that the slurry bed is in a heterogeneous or churn-turbulent flow regime and comprises a dilute phase consisting of fast-rising large bubbles of gaseous reactants, and, possibly gaseous product, which traverse the reaction zone or slurry bed virtually in a plug flow manner, and a dense phase comprising liquid phase, ie liquid product, solid catalyst particles, and entrained smaller bubbles of gaseous reactants and, possibly, gaseous product.

The disengagement or degassing section of each dowrcomer may thus be such as to allow for the bulk of gas bubbles larger than a selected size, eg about 3 mm or greater in diameter, to escape from the fluidised slurry that enters the downcomer. For this purpose, the diameter of the degassing section may be sized such that the downward slurry flow in the degassing section is lower than that of the rise velocity of a selected bubble size, eg 3 mm bubble size. The cross-sectional area of the degassing section of each downcomer in a particular downcomer region may be between 2% and 50%, preferably between 6% and 25%, of the reaction zone cross-sectional area in that downcomer region. The vertical height of the degassing section may be sized to allow sufficient time for gas bubbles larger than said selected size to rise out of the degassing section. This height may typically be between 0,23 m and 0,61 m, but is preferably between 0,31 m and 0,51 m.

The transport section of each downcomer serves to transport the degassed slurry to a lower point in the reactor. The slurry flow through the downcomer is caused by the density difference between the partially or completely degassed slurry in the transport section of the downcomer and the aerated slurry on the outside of the downcomer. Provided that efficient degassing of the "dilute" gas phase takes place in the degassing section, the length and the internal diameter of the transport section are the main characteristics of the downcomer determining the slurry flow rate achievable in the downcomer at a particular set of operating conditions. This is due to the fact that the length and internal diameter of the transport section determines the friction loss in the downcomer. The slurry flow rate achieved in the downcomer is a balance between the density driving force (caused by said density difference) and the friction loss in the transport section as well as pressure loss, due to entrance and exit effects for the transport section. The entrance and exit effects are a function only of the diameter of the transport section.

The slurry flow rate in the downcomer should be below about 5 m/s to prevent both erosion of the downcomer pipe and physical degradation of the catalyst in the slurry. The slurry flow rate inside the downcomer may be between 0,5 m/s and 10 m/s, but is preferably between 2 m/s and 5 m/s. The minimum flow rate in the downcomer is set such that the upward superficial liquid velocity in the reaction zone of the reactor is sufficient to prevent significant catalyst settling ie sufficient to maintain the slurry bed in a state of turbulence or suspension, as hereinbefore described. The upward superficial liquid velocity on the outside of the downcomer may be between 0,5 cm/s to 10 cm/s, but preferably between 2 cm/s to 4 cm/s.

The total length of the transport section of the downcomer may be between 0,3 m and 30 m, preferably between 4 m and 15 m.

While each downcomer will normally be located entirely within the slurry bed ie inside the reactor, with the degassing section typically aligned axially with the transport section, the transport section and, optionally, part of the degassing section can, instead, be located outside the reactor, with the lower outlet end of the transport section and at least the upper inlet end of the degassing section then, however, located inside the reactor in the slurry bed or the slurry bed zone.

In a reactor with a relatively large cross-sectional area, a number of downcomers positioned at various locations through the cross-section of the reactor to achieve the required upward superficial liquid velocity, without exceeding the maximum internal flow rate as specified above, can be used in each of the downcomer regions. Similarly, in a relatively long reactor, a number of shorter downcomers can be used in more than two downcomer regions spaced vertically along the length of the reactor.

The positions of the bottom outlets of the downcomers may be located such that impingement of degassed slurry onto the reactor wall or reactor internals is minimised. Such impingement could lead to erosion or physical degradation of catalyst over a period of time. The positions of the downcomer outlets relative to that of the gas inlet, which is typically connected to a sparger distribution system, should be such that the even distribution of gas into the slurry bed is not adversely affected.

Settling of catalyst in the downcomers is to be avoided. Thus, the angles of the downcomer sections or components, particularly these of the connecting components, should not exceed the angle of repose of the slurry.

The invention will now be described in more detail with reference to the accompanying diagrammatic drawings and the subsequent non-limiting examples.

BRIEF DESCRIPTION OF DRAWINGS

In the drawings,

Referring to FIG. 1, reference numeral 10 generally indicates an installation according to a first aspect of the invention for producing liquid and gaseous products from gaseous reactants.

Figure 1:
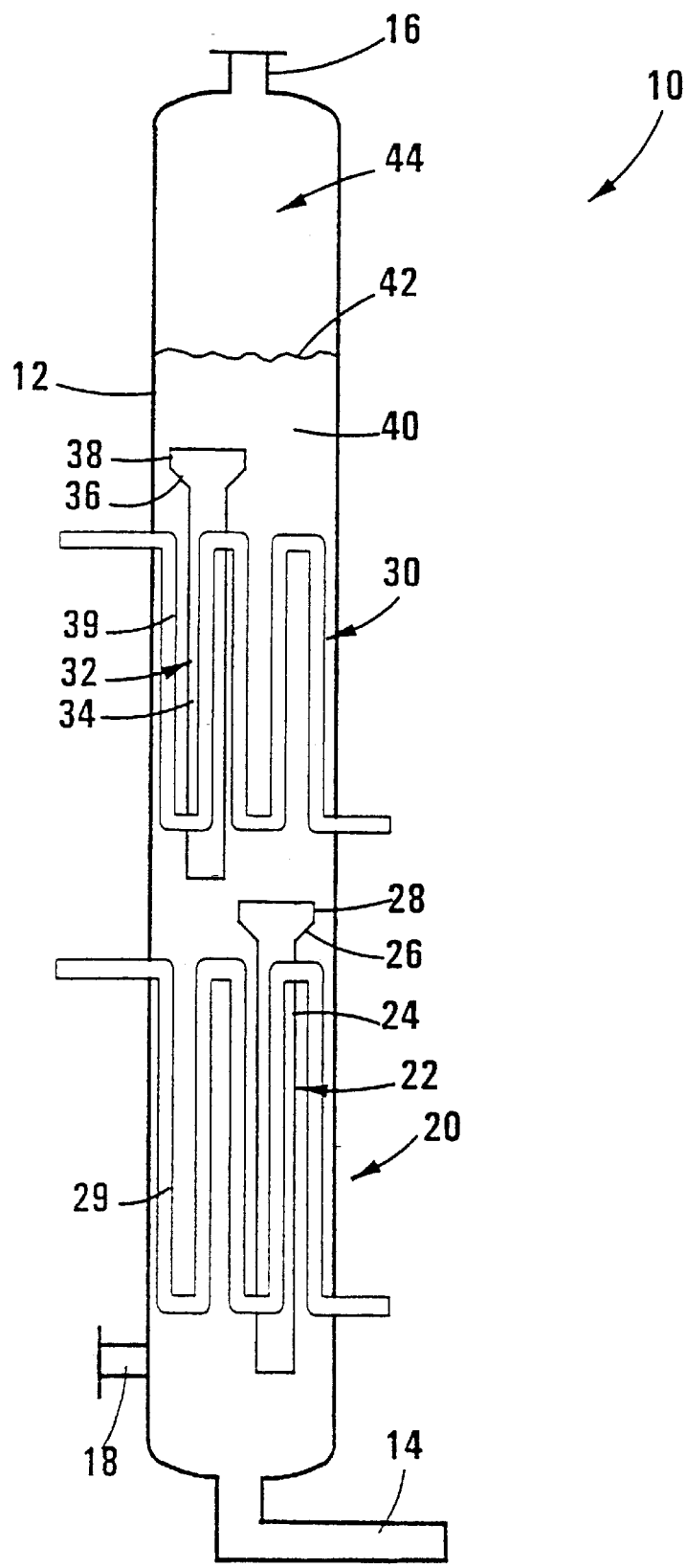
FIG. 1 shows a longitudinal sectional view of an installation according to a first aspect of the invention, for producing liquid and gaseous products from gaseous reactants.

The installation 10 includes an upright cylindrical slurry reactor or bubble column 12, with a gas inlet 14 leading into a gas distributor (not shown) inside the reactor and a gas outlet 16 leading from the top of the reactor. Liquid product outlets 18 lead from the reactor 12 at any convenient level.

The reactor 12 includes a first downcomer region, generally indicated by reference numeral 20. The downcomer region 20 includes a downcomer, generally indicated by reference numeral 22. A downcomer 22 includes a cylindrical transport section 24 of relatively small diameter, an outwardly flaring connecting component 26 at the upper end of the transport section 24, and a larger diameter degassing section 28, the lower end of which is connected to the connecting component 26. The upper end of the degassing section 28 thus provides an inlet for slurry, while the lower end of the transport section 24 provides a slurry outlet. A cooling coil 29 is also provided in the downcomer region 20.

The reactor 12 also includes a second downcomer region, generally indicated by reference numeral 30. The downcomer region 30 includes a downcomer, generally indicated by reference numeral 32. The downcomer 32 also includes a transport section 34 of relatively small diameter, an outwardly flaring connecting component 36 at the upper end of the transport section 34, and a degassing section of relatively large diameter at the upper end of the transport section 34. The lower end of the degassing section 38 is thus connected to the connecting component 36. The upper end of the degassing section 38 provides a slurry inlet, while the lower end of the transport section 34 provides a slurry outlet. A cooling coil 39 is also provided in the downcomer region 30.

The lower end of the downcomer 32 is spaced with vertical clearance from the upper end of the downcomer 22. Furthermore, the downcomer 32 is not aligned axially with the downcomer 22. In other words, the downcomer 32 is staggered relative to the downcomer 22 when the reactor 12 is seen in plan view.

Figure 2:
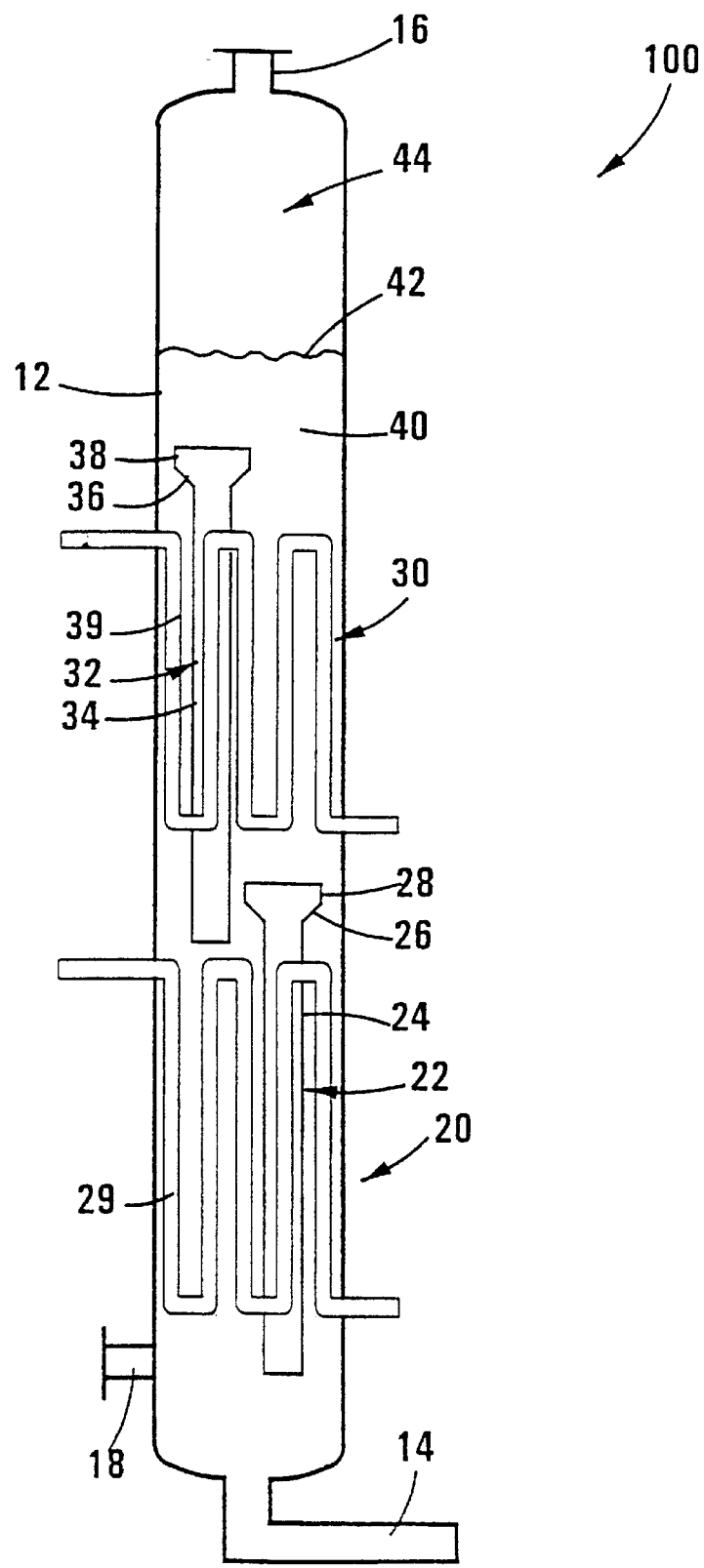
FIG. 2 shows a similar longitudinal sectional view of an installation according to a second aspect of the invention, for producing liquid and gaseous products from gaseous reactants.

Referring to FIG. 2, reference numeral 100 generally indicates an installation according to a second aspect of the invention, for producing liquid and gaseous products from gaseous reactants.

Parts of the installation 100 which are the same or similar to those of the installation 10 of FIG. 1, are indicated with the same reference numerals.

The reactor 12 of the installation 100 is substantially the same as the reactor 12 of the installation 10, save that the lower end of the downcomer 32 overlaps vertically with the upper end of the downcomer 22.

In use, in FIGS. 1 and 2, synthesis gas comprising mainly carbon monoxide and hydrogen as gaseous reactants, is fed into the bottom of the reactor 12 through the gas inlet 14, the gas typically being uniformly distributed through a sparger system (not shown) inside the reactor. The gaseous reactants pass upwardly through a slurry bed 40 comprising Fischer-Tropsch catalyst particles, typically an iron or cobalt based catalyst, suspended in liquid product. The slurry bed is operated to have a normal level 42 above the second downcomer region 30, with a head space 44 being provided above the slurry bed. As the synthesis gas bubbles through the slurry bed, the gaseous reactants therein react catalytically to form liquid product, which thus forms part of the slurry bed 40. From time to time, or continuously, liquid phase comprising liquid product is withdrawn through the outlet 18, with catalyst particles having being separated from the liquid product in a suitable internal filtration system (not shown). Alternatively, the filtration system may be located externally to the reactor, with an additional system (not shown) to return the separated catalyst particles to the reactor then being provided.

Some slurry continuously passes downwardly through the downcomers 32, 22, thereby to achieve uniform redistribution of catalyst particles within the slurry bed 40, and also to ensure uniform heat distribution throughout the slurry bed, as also described in more detail hereunder.

The reactor 12 is operated so that the slurry bed 40 thereof is in a heterogeneous or churn-turbulent flow regime and comprises a dilute phase consisting of fast-rising larger bubbles of gaseous reactants and gaseous product which traverse the slurry bed virtually in plug flow fashion, and a dense phase which comprises liquid product, solid catalyst particles and entrained smaller bubbles of gaseous reactants and gaseous product.

The dense phase; even in the absence of the downcomers 32, 22, experiences a considerable degree of backmixing. Dynamic gas disengagement experiments can be used to determine the gas voidage in the dilute and dense phases. The dense phase gas voidage is practically independent of the reactor column diameter. On the other hand, the dilute phase gas voidage decreases with increasing diameter of the reactor 12.

The Applicant has established that the dependence of the dilute phase gas voidage on column diameter is limited to column diameters less than a maximum value which is of the order of 0,5 m. For example, practically the same gas voidage or gas hold-up has been measured for reactors with diameters of 0,87 m to 5,0 m.

From dynamic gas disergagement experiments as discussed in Van Vuure, D. S., "Hydrodynamic studies on slurry bubble column", CSIR, CENER 8840 (1988), it does not appear to be feasible to design the degassing sections 38, 28 of the downcomers 32, 22 respectively to degass a significant proportion of the dense phase small gas bubbles. The degassing sections will, however, easily separate the dilute phase large gas bubbles, typically bubbles having a diameter greater than about 3 mm.

The gas voidage in the transport sections 34, 24 of the downcomers 32, 22 will be the dense phase gas voidage and this can be determined by bed collapse experiments. In specific examples conducted on a Works Pilot Plant, it was possible to infer the gas voidage from a pressure drop measurement on the transport section of a downcomer. This measurement confirmed that the gas voidage in the downcomer is independent of the gas velocity in the reactor. The idense phase gas voidage is a function of the fluid properties and the catalyst concentration. There are no reliable calculation methods to predict the dense phase gas voidage, and this must be determined by experiment as, for example, described above. The values of the dense phase gas voidage in the tests done was between 0,25 and 0,35, typically 0,3.

An acceptable calculation method to determine a design value for the slurry velocity in the transport section has been derived. By taking the entrance, exit and pipe wall friction losses the following expression is obtained:

$$u = \sqrt{\frac{\alpha\left(1 - \frac{\rho_B g \cdot L}{\Delta P \cdot 1000}\right)}{1 - \frac{L\alpha\rho_B f'}{\Delta P \cdot 2000 \cdot d_d}}} \quad \text{where} \tag{1}$$

$$\alpha = \frac{-2gh}{\beta^2 - 2.32 - \frac{f'h}{d_d}} \quad \text{and} \tag{2}$$

-continued $$\beta = \frac{d_d}{d_e} \quad (3)$$

u=Slurry velocity, m/s
ρB=Gassed slurry bed density (kg/m³)
g=Gravitational Constant (m/s²)
ΔP=Pilot Plant Measured pressure difference (kPa)
L=Distance between pilot plant pressure taps (m)
f=pipe wall friction factor
$d_d$=Downcomer transport section diameter (m)
$d_e$=Downcomer disengagement section diameter (m)
h=Downcomer length (m)

This calculation is considered to be an approximation that is sufficiently accurate to provide a reliable design if the calculated velocity is determined to be in the preferred range of 2 m/s to 5 m/s. More sophisticated calculation techniques, such as computational fluid dynamic (CFD) modelling, can be used to optimize the design and layout of the downcomers.

By using downcomers at different vertical elevations, the degree of backmixing of dense phase gas can be decreased, thus enhancing the conversion performance of the reactor. The backmixing of small bubbles outside the downcomer is believed to have no significant consequence since there is rapid mass transfer between the gas and slurry phase for these small bubbles. This has been confirmed by tracer experiments, using a 0,87 m diameter reactor, which show that, in the absence of downcomers, the gas flow through the slurry bed reactor is essentially plug flow, with gas phase Peclet numbers higher than 20 at superficial gas velocities ranging from 13 to 60 cm/s. However, when prevented from contacting the bulk of the slurry while passing down the downcomer, they can contribute to significant backmixing of gas from regions closer to the exit concentration to regions closer to the entrance concentrations. This effect can be decreased by using downcomers at different vertical elevations.

EXAMPLE 1

A Fischer-Tropsch slurry phase reactor with an internal diameter of 0,87 m and a bed height of 18 m, was fitted with a downcomer having an overall length of 14,7 m, a disengagement section diameter (ID) of 0,354 m and 0,102 m (ID) diameter transport section. A ΔP of 33,35 kPa was measured with pressure taps located 6 m apart along the downcomer. The bulk density in the reactor was 470 kg/m³. If a wall friction factor of 0,02 is assumed the following values were calculated:

For equation (3):

β=0,289

For equation (2):

α=56,42

The slurry downward velocity in the transport section of the downcomer was then calculated, by using equation (1), as being 4,24 m/s. This velocity is lower than the preferred upper velocity limited of 5 m/s. The design of the downcomer thus renders it suitable for use as the downcomer 22 or 32 in the installations 10, 100 according to the invention.

EXAMPLE 2

A Fischer-Tropsch slurry phase reactor with an internal diameter of 0,87 m and a bed height of 18 m was fitted with two downcomers 32 and 22 having overall lengths of 7 m and 8,3 m respectively. Both downcomers had disengagement sections of 0,354 diameter (ID) and 0,102 diameter (ID) transport sections. The two downcomers overlapped by 1 m so that the reactor configuration was in accordance with that of FIG. 2.

A Δp of 35,7 kPa was measured over pressure taps situated 6 m apart along the downcomer 32. The bulk density in the reactor was 470 kg/m³. If a wall friction factor of 0,02 is assumed, the following values were calculated:

For equation (3):

β=0,289

For equation (2)

α=38,05

The slurry downward velocity in the transport section of the downcomer 32 was then calculated, by using equation (1), as 3,49 m/s. This velocity is lower than the preferred upper velocity limit of 5 m/s.

A Δp of 35,2 was measured over pressure taps situated 6 m apart along the downcomer 22. The bulk density in the reactor was 470 kg/m³. If a wall friction factor of 0,02 is assumed, the following values were calculated:

For equation (3):

β=0,289

For equation (2):

α=42,14

The slurry downward velocity in the transport section of the downcomer 22 was then calculated, by using equation (1), as 3,67 m/s. This velocity is lower than the preferred upper velocity limit of 5 m/s.

The installations 10, 100 are suitable for carrying out highly exothermic, three phase, catalytic reactions, particularly Fischer-Tropsch reactions. By virtue of the downcomers 22, 32 which are unrestricted, eg they do not have baffles at the lower ends of their transport sections, uniform redistribution of the catalyst in the slurry reactor, and hence more effective use of the catalyst is obtained.

Slurry phase type reactors provide improved heat transfer characteristics for exothermic reactions such as Fischer-Tropsch reactors, due to the bubbling of gas into the reactor vessel keeping the catalyst particles in the suspension. The heat transfer coils inside the reactor vessel also absorb the heat generated by the exothermic reaction. Uniform distribution of heat in slurry bed reactors used for organic synthesis involving the Fischer-Tropsch reaction with a very active particulate catalyst, such as cobalt, and which is thus even more exothermic, however provides a problem.

The Applicant has thus surprisingly found that the use of downcomers 22, 32 at different levels assists in solving the problem of uniform heat distribution for such highly exothermic reactors. The use of downcomers at different levels in accordance with the invention results in a uniform temperature level (within 5° C.) throughout the slurry phase in any diameter commercial slurry phase reactor.

The use of a downcomer for the redistribution of heat has, as mentioned, the additional advantage of uniform redistribution of particulate catalyst, but also has the disadvantage of back flow of gas in the form of small bubbles from the inlet at the top of the downcomer to the outlet at the bottom of the downcomer. However, the applicant has also surprisingly found that by selecting the specific downcomer arrangement, in accordance with the present invention, this disadvantage is at least reduced, rendering a mere effective operation of the slurry bed reactor. By means of gas tracer experiments, Peclet numbers in excess of 3 were measured for the installation 100 (as described in Example 2) at superficial gas velocities ranging from 15 to 30 cm/s at an operating pressure of 20 bar. The present invention also solves other disadvantages known to occur in slurry bed reactors, even when using a conventional single downcomer configuration, such as.:

i) In slurry bed reactors fitted in known fashion with a single downcomer, high temperatures are experienced at the bottom of the slurry bed reactor in the event that the slurry phase level drops below the top of the downcomer; this is avoided with the plurality of downcomers in accordance with the invention since such high temperatures are not experienced should the slurry level 42 drop below the upper end or top of the downcomer 32 in the second downcomer region 30; and ii) High slurry velocities in the downcomer transport sections, which would otherwise result in erosion of the dowrcomer and/or catalyst attrition, are at least reduced by using the downcomers in the vertically spaced downcomer regions in accordance with the invention.

What is claimed is:

1. A process for producing liquid and, optionally, gaseous products from gaseous reactants, which process comprises the steps of:

feeding, at a low level, gaseous reactants into a slurry bed of solid particles suspended in a suspension liquid;

allowing the gaseous reactants to react as they pass upwardly through the slurry bed, thereby to form liquid and, optionally, gaseous products, with the gaseous reactants and any gaseous product assisting in maintaining the solid particles in suspension in the suspension liquid, and with the liquid product forming, together with the suspension liquid, a liquid phase of the slurry bed;

allowing any gaseous product and unreacted gaseous reactants to disengage from the slurry bed into a head space above the slurry bed;

allowing slurry to pass downwardly from a high level in the slurry bed to a lower level thereof, through at least one downcomer located in a first downcomer region of the slurry bed, as well as through at least one further downcomer located in a second downcomer region of the slurry bed, with the second downcomer region being spaced vertically with respect to the first downcomer region, thereby to redistribute solid particles within the slurry bed;

withdrawing any gaseous product and unreacted gaseous reactants from the head space; and withdrawing liquid phase from the slurry bed, to maintain the slurry bed at a desired level.

2. A process according to claim 1, wherein the solid particles are catalyst particles for catalyzing the reaction of the gaseous reactants into the liquid product, and, when applicable, the gaseous product; and wherein the suspension liquid is the liquid product, with the slurry bed being contained in a reaction zone of a slurry reactor or bubble column using a three phase system comprising solid catalyst particles, liquid product, and gaseous reactants.

3. A process according to claim 2, wherein the gaseous reactants react catalytically in the slurry bed to form liquid hydrocarbon product and gaseous hydrocarbon product by means of Fischer-Tropsch synthesis, with the gaseous reactants being in the form of a synthesis gas stream comprising mainly carbon monoxide and hydrogen.

4. A process according to claim 3, wherein the catalyst is an iron-based Fischer-Tropsch catalyst, a cobalt-based Fischer-Tropsch catalyst, or an iron- and cobalt-based Fischer-Tropsch catalyst, with the catalyst particles having a particle size range such that no catalyst particles are greater than 300 microns and less than 5% by mass of the catalyst particles are smaller than 22 microns.

5. A process according to claim 3, wherein each downcomer comprises a lower transport section and an upper disengagement section of greater cross-sectional area than the transport section, with an outwardly upwardly flaring connecting component connecting the disengagement section to the transport section.

6. A process according to claim 5, wherein the steps are operated such that the slurry bed is in a heterogeneous or churn-turbulent flow regime and comprises a dilute phase consisting of fast-rising large bubbles of gaseous reactants and gaseous product, which traverse the reaction zone or slurry bed virtually in a plug flow manner, and a dense phase comprising liquid phase, solid catalyst particles, and entrained smaller bubbles of gaseous reactants and gaseous product.

7. A process according to claim 6, wherein the disengagement section of each downcomer permits the bulk of gas bubbles larger than 3 mm in diameter to escape from the fluidized slurry that enters the downcomer, with the diameter of the disengagement section being such that the downward slurry flow in the disengagement section is lower than that of the rise velocity of 3 mm bubble size.

8. A process according to claim 7, wherein the cross-sectional area of the disengagement section of each downcomer is between 2% and 50% of the reaction zone cross-sectional area the downcomer region in which the downcomer is located with the vertical height of the disengagement section being between 0.23 m and 0.61 m to allow sufficient time for the 3 mm gas bubbles to rise out of the disengagement section.

9. A process according to claim 5, wherein the slurry flow rate in the downcomer(s) is(are) below about 5 m/s to inhibit both erosion of the downcomer pipe and physical degradation of the catalyst in the slurry.

10. A process according to claim 9, wherein the slurry flow rate inside the downcomer(s) is(are) between 2 m/s and 5 m/s.

11. A process according to claim 5, wherein the upward superficial liquid velocity on the outside of the downcomer(s) is(are) between 2 cm/s to 4 cm/s.

* * * * *

UNITED STATES PATENT AND TRADEMARK OFFICE
CERTIFICATE OF CORRECTION

PATENT NO. : 6,201,031 B1
DATED : March 13, 2001
INVENTOR(S) : Andre Peter Steynberg et al.

It is certified that error appears in the above-identified patent and that said Letters Patent is hereby corrected as shown below:

Title page,
Item [75], "Andr"" should read -- Andre --.

Signed and Sealed this

Eleventh Day of December, 2001

Attest:

Nicholas P. Godici

NICHOLAS P. GODICI
Attesting Officer      Acting Director of the United States Patent and Trademark Office